(12) United States Patent
Sattler et al.

(10) Patent No.: US 9,149,979 B2
(45) Date of Patent: Oct. 6, 2015

(54) METHOD FOR PRODUCING A REAGENT CONTAINER ASSEMBLY AND REAGENT CONTAINER ASSEMBLY

(75) Inventors: Stephan Sattler, Starnberg (DE); Reinhold Kraemer, Peissenberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 557 days.

(21) Appl. No.: 13/152,601

(22) Filed: Jun. 3, 2011

(65) Prior Publication Data
US 2012/0141339 A1 Jun. 7, 2012

Related U.S. Application Data

(63) Continuation of application No. PCT/EP2009/066422, filed on Dec. 4, 2009.

(30) Foreign Application Priority Data
Dec. 5, 2008 (EP) .................................... 08021175

(51) Int. Cl.
| | |
|---|---|
| *B29C 65/02* | (2006.01) |
| *B01L 3/00* | (2006.01) |
| *B29C 65/08* | (2006.01) |
| *B29C 65/16* | (2006.01) |
| *B29C 65/00* | (2006.01) |
| *G01N 35/10* | (2006.01) |
| *G01N 35/00* | (2006.01) |

(52) U.S. Cl.
CPC ............... *B29C 65/02* (2013.01); *B01L 3/527* (2013.01); *B29C 65/08* (2013.01); *B29C 65/16* (2013.01); *B29C 66/1122* (2013.01); *B29C 66/137* (2013.01); *B29C 66/21* (2013.01); *B29C 66/32* (2013.01); *B29C 66/326* (2013.01); *B29C 66/43* (2013.01); *B29C 66/54* (2013.01); *B29C 66/543* (2013.01); *B29C 66/545* (2013.01); *B29C 66/81267* (2013.01); *B29C 66/81427* (2013.01); *B01L 2200/12* (2013.01); *B01L 2200/148* (2013.01); *B01L 2300/024* (2013.01); *B29C 66/30221* (2013.01); *B29C 66/81422* (2013.01); *B29C 66/83221* (2013.01); *G01N 35/1002* (2013.01); *G01N 2035/00673* (2013.01); *G01N 2035/00851* (2013.01)

(58) Field of Classification Search
CPC ............................... B29C 65/02; B01L 3/527
USPC .................................. 422/562, 554; 426/120
See application file for complete search history.

(56) References Cited

U.S. PATENT DOCUMENTS

| | | | |
|---|---|---|---|
| 5,251,778 A | 10/1993 | Eggl | |
| 5,862,934 A * | 1/1999 | Sattler et al. | ................. 220/23.4 |

(Continued)

FOREIGN PATENT DOCUMENTS

| | | | |
|---|---|---|---|
| EP | 0692308 A2 | 1/1996 | |
| EP | 1538447 A2 | 6/2005 | |

(Continued)

*Primary Examiner* — Sally Merkling
(74) *Attorney, Agent, or Firm* — Dinsmore & Shohl LLP

(57) ABSTRACT

Embodiments directed to a process for producing a reagent container assembly made of plastic and a reagent container assembly are disclosed. The process may comprise: assembling a group of particular reagent containers, and joining the reagent containers to form the reagent container assembly where at least two of the reagent containers are permanently joined together by at least one welding process.

10 Claims, 9 Drawing Sheets

(56) References Cited

U.S. PATENT DOCUMENTS

| | | | |
|---|---|---|---|
| 2002/0110623 A1* | 8/2002 | Rebhorn et al. | 426/120 |
| 2005/0170356 A1* | 8/2005 | Kureshy et al. | 435/6 |
| 2008/0035636 A1 | 2/2008 | Grant et al. | |
| 2009/0058617 A1* | 3/2009 | Wu et al. | 340/10.41 |

FOREIGN PATENT DOCUMENTS

| | | | | |
|---|---|---|---|---|
| FR | 2261931 A1 | 9/1975 | | |
| FR | 2532240 A1 | 3/1984 | | |
| FR | 2697811 A1 | 5/1994 | | |
| FR | 2710327 A1 | 3/1995 | | |
| FR | 2615786 A1 | 12/1998 | | |
| GB | 1469043 | 3/1977 | | |
| JP | 2002-37262 A | 2/2002 | | |
| JP | 2008-180639 | 8/2008 | | |
| JP | 2008180639 | * 8/2008 | | G01N 35/02 |
| NL | 7802703 A | 9/1978 | | |
| WO | 2005/110872 A2 | 11/2005 | | |
| WO | 2008/009821 A1 | 1/2008 | | |

* cited by examiner

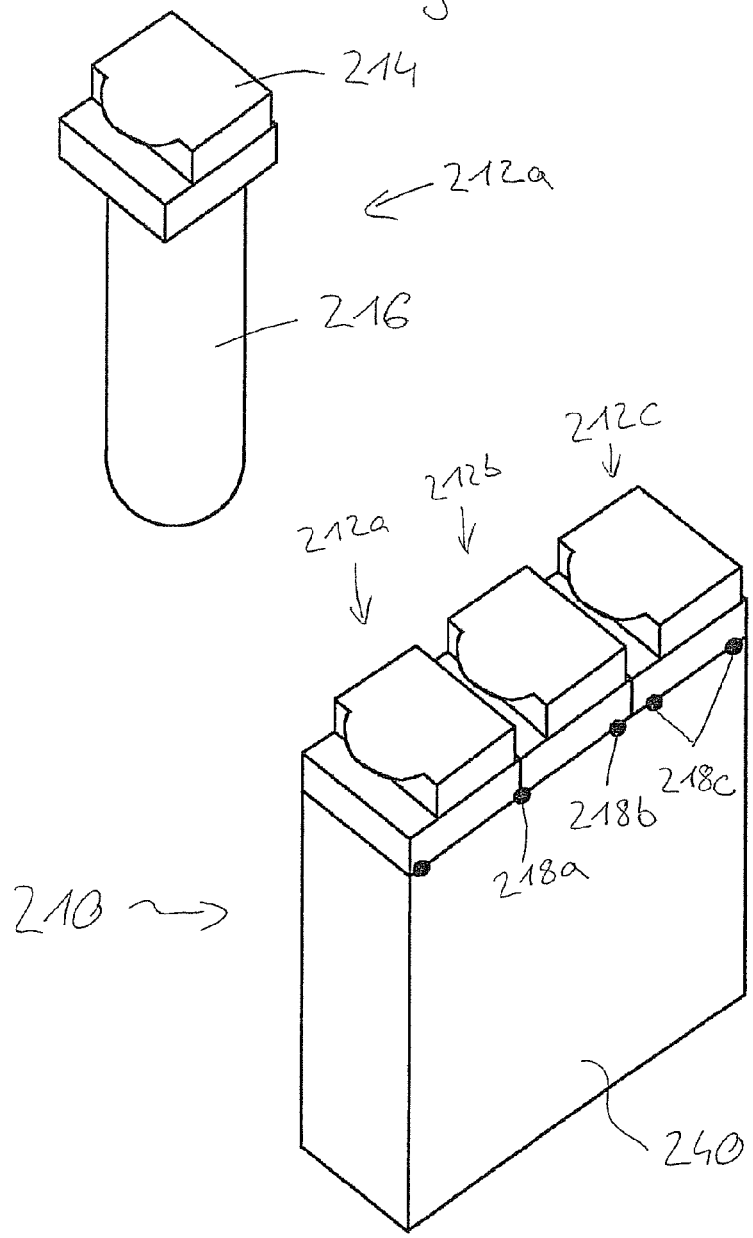

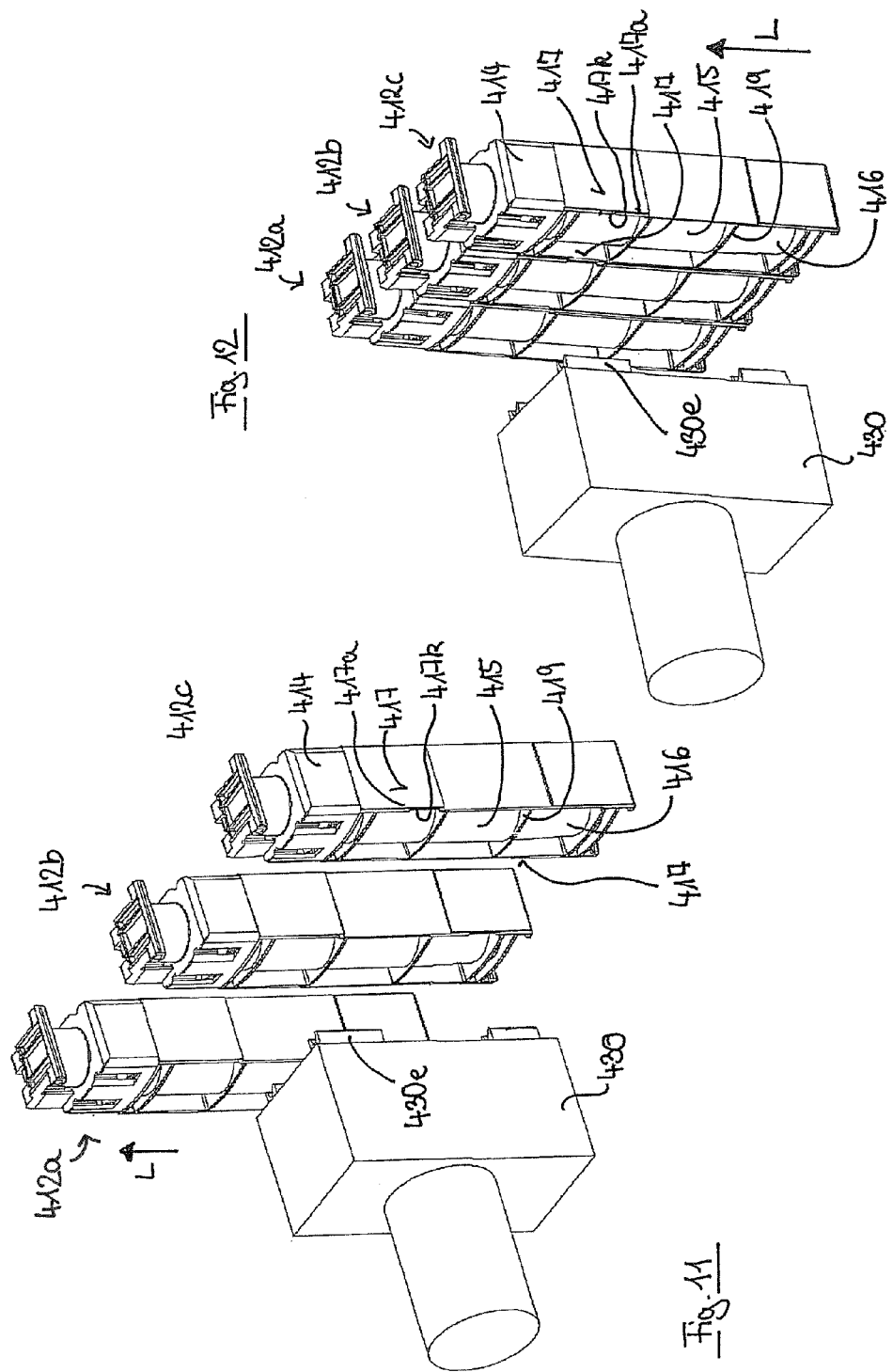

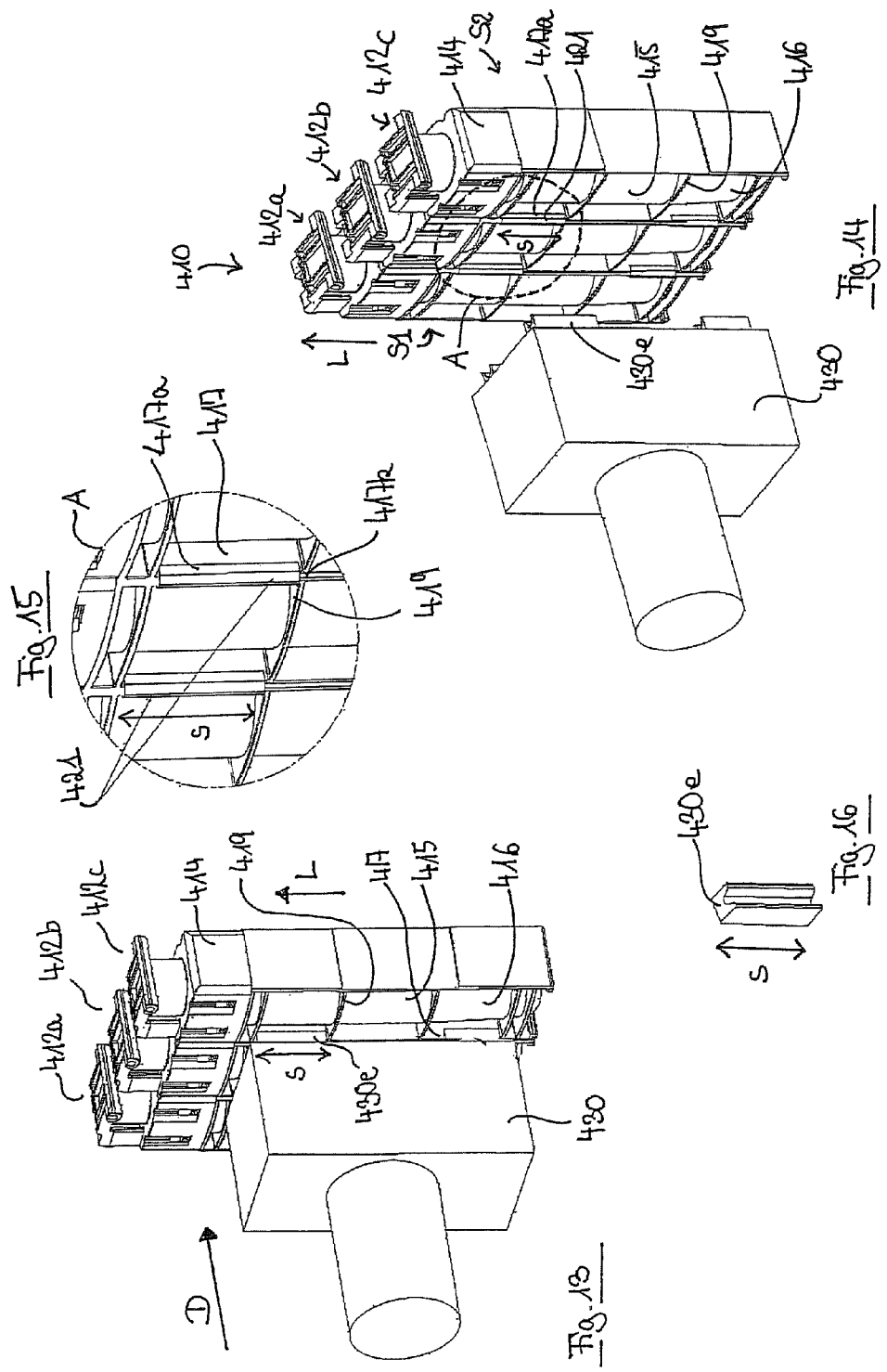

METHOD FOR PRODUCING A REAGENT CONTAINER ASSEMBLY AND REAGENT CONTAINER ASSEMBLY

CROSS-REFERENCE TO RELATED APPLICATIONS

This application is a continuation of International application PCT/EP2009/066422, filed Dec. 4, 2009, which claims priority to EP application 08021175.8, filed Dec. 5, 2008.

TECHNICAL FIELD

The present disclosure concerns a process for producing a reagent container assembly made of plastic which may comprise assembling a group of particular reagent containers, and joining the reagent containers to form the reagent container assembly.

BACKGROUND

Reagent container assemblies are used in automated analyzers for clinical analytics. In particular, a plurality of reagent containers have to be mechanically handled in such analyzers. For practical reasons, groups of reagent containers are already assembled during the production process into reagent container assemblies that can be collectively handled as a unit. For example, a reagent container assembly may comprise a group of particular reagent containers which have been filled with the reagents or auxiliary substances that are required for a predetermined analytical process. If it is intended to carry out the analytical process using an analyzer, then it is sufficient to only insert such a reagent container assembly into the analyzer instead of several individual reagent containers.

SUMMARY

In one embodiment, a process for producing a reagent container assembly made of plastic is disclosed. The process may comprise: assembling a group of particular reagent containers; and joining the reagent containers to form the reagent container assembly such that at least two of the reagent containers are joined together by at least one welding process.

In another embodiment, a reagent container assembly is disclosed. The assembly may comprise at least two plastic reagent containers that are attached to one another, and wherein the reagent containers are permanently joined together by at least one fusion welding point.

BRIEF DESCRIPTION OF THE DRAWINGS

FIG. 8 shows an embodiment of a reagent container with a rounded bottom surface.

FIG. 9 shows a further embodiment of a reagent container assembly comprising reagent containers arranged jointly in a stand.

FIG. 11 shows a further embodiment of reagent containers which can be welded by ultrasonic welding using a special multiple sonotrode that is also shown to form a further embodiment of a reagent container assembly.

FIG. 12 shows the reagent containers of FIG. 11 after positioning for ultrasonic welding.

FIG. 13 shows the reagent containers of FIG. 12 during the ultrasonic welding.

FIG. 14 shows the reagent containers of FIG. 13 as a reagent container assembly after the ultrasonic welding.

FIG. 15 shows an enlargement of a section of FIG. 14.

FIG. 16 shows another perspective and enlarged diagram of one of the welding dies of the multiple sonotrode used to manufacture the reagent container assembly shown in FIG. 14.

DETAILED DESCRIPTION

Figure 1:
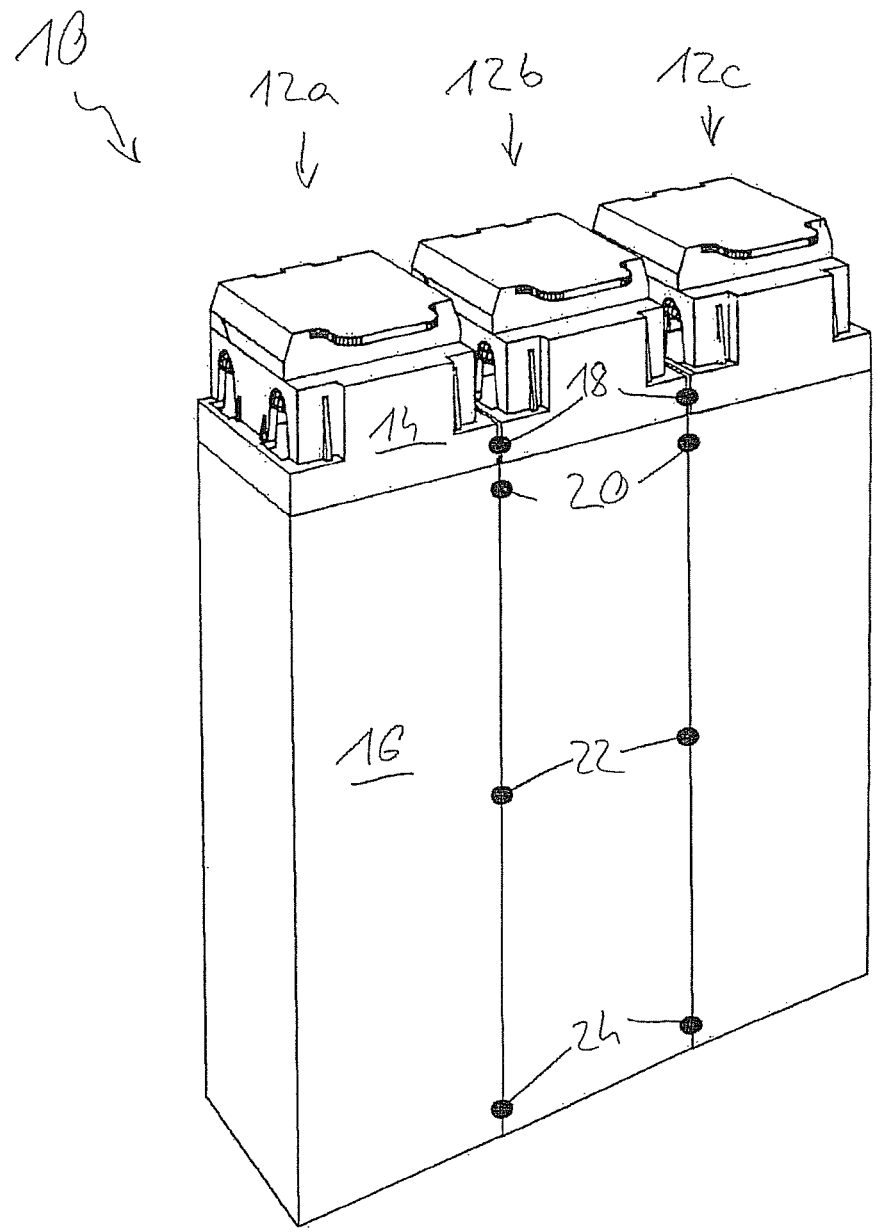
FIG. 1 shows a first embodiment of a reagent container assembly comprising reagent containers that are directly welded together in a perspective view.

Individual reagent containers of a reagent container assembly are usually already filled with reagents before the assembly. However, it cannot be ruled out that a reagent container is not yet filled when the reagent container assembly is assembled. It may also be necessary either to coat individual reagent containers before filling or to manufacture them from a different material than the other reagent containers of the reagent container assembly. Even if a coated reagent container is not filled with a reagent until the reagent container assembly has been joined, the coating preferably already occurs before the assembly of the reagent containers.

Normally, the various reagents which are intended for a certain reagent container assembly are produced either at different locations or at different times. If an already original one-piece reagent container assembly comprising several reagent containers had to be filled with these reagents, then it would have to be transported already partially filled from one location to another or stored partially filled. Clearly, it is simpler to transport and store individual reagent containers.

Since the composition of a certain reagent can vary due to the production process, it may under certain circumstances be necessary to adapt the reagents of a reagent container assembly to one another. Again, it is simpler to use individual reagent containers which, after filling, are joined to one another to form a reagent container assembly. In this process, a first reagent is produced and filled into individual reagent containers without intermediate storage. After an exact analysis of the first reagent, a second reagent which is adapted (calibrated) to the first reagent is produced and filled into further individual reagent containers without intermediate storage. One of the reagent containers filled with the first reagent is then joined to a reagent container filled with the second reagent to form a reagent container assembly which contains the two matching reagents.

These examples show that for logistic reasons it is disadvantageous to produce an arrangement of containers comprising several chambers in one piece corresponding to the reagent container assembly and afterwards to fill the chambers with different reagents or auxiliary substances.

It is therefore much more practical to fill the reagents into separate reagent containers and then assemble and join these containers as required to form the necessary reagent container assemblies.

Within the scope of the present application the term reagent is also intended to encompass auxiliary substances such as carrier particles, e.g., beads.

In a production process known from EP 0 692 308 A2 a large number of individual reagent containers made of polyolefins such as, e.g., polypropylene or polyethylene are produced and subsequently filled with different reagents. The particular reagent containers that are intended for a reagent container assembly are mechanically joined by a connecting frame. The connecting frame and the reagent containers have joining elements for this purpose in the form of snap closure elements. In the joining process each of the reagent containers is plugged into its predetermined position in the connecting frame, the snap closure elements engage and join the reagent containers to the connecting frame. The reliable mechanical connection of the reagent containers to the connecting frame is a complicated procedure. The connecting frame is a separate component with a relatively complicated shape, the manufacture of which is complicated and cost-intensive.

Furthermore it is disadvantageous that the connecting frame increases the space required for the reagent container assembly in the respective analyzer because it essentially defines the dimensions of the outer contour of the reagent container assembly.

Therefore embodiments of the present invention disclose a process of the type mentioned-above for producing reagent container assemblies faster and more cost-effective.

In one embodiment, a process for producing a reagent container assembly made in particular of thermoplastic plastic comprises:

assembling a group of particular reagent containers, and joining the reagent containers to form the reagent container assembly where at least two of the reagent containers are permanently joined together by at least one welding process.

As use herein, the term "permanent joining of two reagent containers" is understood to mean that the connection cannot be broken without the use of special separating tools such as knives, saws or pincers, or can only be broken by exerting such a force that it would be expected that at least one of the reagent containers would be destroyed in this process or at least damaged in such a way that its function is impaired. This prevents an unintentional detachment of a reagent container from the reagent container assembly, for example, due to breakage during transport.

By welding the at least two reagent containers it is possible to use simply designed reagent containers without the specially formed plug connecting elements. Reagent containers can be produced more rapidly and cost-effectively because the separate connecting frame known from the prior art is no longer necessary. Also the space required for the reagent container assembly is not increased by connecting measures.

As described above it is advantageous for logistical reasons and in order to make the process economical to fill the individual reagents as immediately as possible after their production into individual reagent containers and to subsequently join the filled reagent containers together to form a reagent container assembly.

Hence, the process in another embodiment can comprise a further step in which at least one of the particular reagent containers is filled with a reagent before the reagent containers are connected to form the reagent container assembly. The reagent containers can be capped immediately after the filling process so that the filled and closed reagent containers are firstly stored and can be assembled to form the reagent container assembly at a later time, for example, when all reagents required for a particular test have been produced and filled.

In another embodiment, all reagent containers are assembled to form the reagent container assembly in a filled and optionally capped state; but it is, however, also conceivable that individual reagent containers are not filled until after the assembly in still another embodiment.

Experiments have shown that the permanent welding proposed by the invention of filled or coated reagent containers to form a reagent container assembly does not critically damage the reagent containers or allow them to become leaky. Thus, it was found that the welding process did not change thermally sensitive reagents in the containers or affect their activity. This was simply not to be expected.

Since reagent container assemblies which are used in clinical analytics, and in which reagents are present for a certain analytical process, require reagents that quantitatively and accurately match one another, i.e., calibrated reagents, it is advantageous as described above to fill the individual reagent containers with reagents that are calibrated against one another, i.e., to fill at least one other of the particular reagent containers with at least one other reagent which is calibrated against the one reagent before connecting the reagent containers.

Alternatively, or in addition, a quality control of the individual reagents can be carried out before filling the reagents into the individual reagent containers and welding the reagent containers to form the reagent container assembly.

Calibration of the at least one other reagent against the one reagent can be advantageously integrated into the process according to another embodiment of the invention by carrying it out before filling the at least one other reagent container.

In order to simplify the use of the reagent container assembly, which contain reagents that are calibrated against one another in an analytical system, it is possible to provide the calibration data that is registered when the at least one other reagent is calibrated against the at least one reagent. In such an embodiment, the reagent container assembly can be provided with the calibration data in a form which can be read out by a user or automatically read out by the analytical system.

If it is intended that the calibration data be read out by the user and, for example, entered manually into the analytical system, the information can be provided in the form of a separate data sheet. The data sheet can be enclosed with the reagent container assembly or attached in a suitable manner to the reagent container assembly or provided in an electronic form on a data carrier.

In order to enable the calibration data to be automatically read out by the analytical system, the data can be, for example, attached to the reagent container assembly in the form of a bar code or RFID transponder.

This "labeling" of the reagent container assembly can take place in an advantageous manner on the same machine on which the reagent containers are assembled.

Alternatively, or in addition, it is possible to record lot data of one or more of the reagents in the manner described above, and thus provide the reagent container assembly with this data.

In particular, when at least one spot-welded joint is formed during the welding process, as is proposed for an embodiment of the invention, the heat introduced into the container can be kept to a low level. As used herein, "spot-welded joint" or "spot weld" means a welded joint which is limited to a local area but does not necessarily have to be spot-shaped or circular in the strict mathematical sense. One could, for example, in this case also envisage essentially ellipsoidal or rectangular welded joints.

Alternatively, instead of a spot-welded joint, a weld seam could be generated during the welding process to join the reagent containers which provides a more stable joint. However, in return, such a welding process may put a somewhat greater strain on the containers to be joined than a spot-welded joint.

As described below in more detail, the reagent containers can, however, be designed such that the heat introduced when making welded joints can be kept so low, at least in the area of the reagent container which forms the actual reagent receiver, that damage to the reagent receivers and the reagents filled therein can be avoided during the welding process.

Spot-welded joints have another advantage. In some analytical processes, it is envisaged that one of the reagent containers will be separated from a particular reagent container assembly so that it can be transported to another location independently of the remainder of the reagent container assembly. This requires that the welds joining the reagent container with the remainder of the reagent container assembly be broken. Individual spot-welded joints have less joining stability than a weld seam and can be more easily undone by a simple separating tool.

In another embodiment, preferably at least two of the reagent containers are joined together by at least two welded joints that are at a distance from one another. This ensures that the two containers are joined in a sufficiently stable manner if one of the two welded joints should be damaged.

Under certain circumstances, it may be advantageous if at least two of the reagent containers are joined together by more than two welded joints that are spaced apart, such as welded joints on opposite sides of the reagent container assembly.

The welding process in one embodiment is preferably an ultrasonic welding process. Experiments of the applicant have shown that in ultrasonic welding, pressing the sonotrodes onto the area of the two reagent containers that are to be joined makes the softened plastic flow in such a manner that a bridge joining the two reagent containers is formed without further measures especially when the two reagent containers do not rest tightly against one another in the area of the joint but are rather slightly spaced apart. Alternatively, the welding process can also be another welding process, e.g., a laser welding process.

If desired and in order to provide additional plastic material to join the at least two reagent containers, in another embodiment a material thickening may be provided on at least one reagent container which flows during the welding process. This material thickening also ensures that the area in which the welding takes place does not become thinner than the remainder of the container wall due to the flowing of the thermally softened material.

In order to keep the amount of heat introduced during ultrasonic welding as low as possible, at least in the area of the reagent container that is in direct contact with reagent that has been filled into the container, it may be provided that at least two reagent containers that are to be joined together are used in which each have a plate-shaped connecting wall section with an outwardly protruding plate edge. In this embodiment, the two reagent containers are then arranged before joining in such a manner that the connecting wall sections either rest against one another at least in the area of the plate edges or are essentially parallel to one another with a small spacing. The two reagent containers are then joined by ultrasonic welding with a sonotrode in which the welding dies jointly grip around the two plate edges of the connecting wall sections of the two reagent containers during the welding process. The fact that the plate edges should protrude outwards is intended to mean that they project away from, in particular, the actual reagent receiver and are thus not directly in contact with reagents. The distance between welded areas and, for example, fluid-carrying wall areas of a filled reagent container can be enlarged and the heat introduced into the reagents can be minimized in this manner even though it is possible to generate very stable welding joints by correspondingly long wall sections and welding dies.

Another advantage is that by welding protruding plate edges instead of directly welding wall sections of the container wall that carry liquids or in general reagents, it is possible to drastically reduce or even exclude the risk of creating leakages in the container due to the welding.

The fact that the connecting wall sections run parallel to one another at a small spacing means that their spacing is only sufficiently large enough to enable the two plate edges of the connecting wall sections to be jointly gripped by the welding dies of the sonotrode and thus be joined together by ultrasonic welding.

The welding die in one embodiment is preferably configured in the shape of a rounded V at its longitudinal end which grips around the plate edges so that the two connecting wall sections can be pressed towards the plane of symmetry of the welding die by exerting pressure and thus pressed together. This pressing together increases the mixing of the heated plastic material and thus increases the strength of the joint created by ultrasonic welding.

Furthermore, the joint is formed in a rounded shape by the rounded V shape of the sonotrode. As such, burrs or excess material formed during the welding do not project from the surface of the reagent container assembly or project as little as possible. This simplifies the automatic handling of the reagent container assembly and reduces the risk of injury to a user who handles this reagent container assembly.

In one embodiment, the at least two reagent containers are preferably directly welded together although according to one variant of the process according to the invention it is also conceivable that an additional functional component of the reagent container assembly such as a stand is used to indirectly join the reagent containers.

For example, the reagent containers can be arranged in a common stand and welded with the stand. In particular, reagent containers which have the usual rounded shape for test tubes at their lower end and which cannot stand alone with this end on a flat support can be arranged in a stand such that the reagent container assembly formed from these reagent containers and the stand can be placed on a flat surface.

It is particularly effective when at least two reagent containers and the stand are welded together with at least one common joint. This allows the number of required welded joints to be reduced.

It is also possible that one of the reagent containers to be welded has more than one chamber for reagents. The reagent container with more than one chamber could in this connection be formed in a first welding process in which two reagent containers each having one chamber are welded together. In a subsequent welding process, the reagent container having more than one chamber can then be joined to another reagent container to form the reagent container assembly.

Usually pipetting devices, or even a mixing device in the form of a blender, are inserted into openings of the reagent containers during an analytical process in one of the above-mentioned analyzers. The exact positioning of the openings of the reagent containers relative to the analyzer is particularly important when the diameter of the blender is only marginally smaller than the opening of the corresponding reagent container. If the reagent containers are only pressed together when they are joined, the overall width of the reagent container assembly can vary due to production-related tolerances in the width of the individual reagent containers. If reagent container assemblies of such different widths are arranged in a holder of the analyzer, the amount of play of the reagent container within the holder can result in the opening of the reagent container, especially if the reagent container assembly has turned out to be relatively short. The opening of the reagent container far removed from a set position into which the blender should be inserted may result in the blender touching the edge of the opening which can lead to damage of the blender and/or the opening.

In order to avoid the above mentioned problem it is proposed in another embodiment that the reagent containers are assembled and welded together in a positioning device relative to positioning stops of this positioning device. For this purpose, the positioning devices have a predefined spacing which determines the overall width of the reagent container assembly that is formed. The two outer reagent containers of a reagent container assembly are for this purpose placed against the positioning stops in order to position them before the welding process. The reagent container assembly that is formed obtains a pre-defined width and the openings of the two outer reagent containers can be accurately positioned in an analyzer.

Certain reagent containers have a cover member which can be formed from a plastic that is different from that of the remainder of the reagent container. Under certain circumstances the plastic of the cover member may be more suitable for being welded or could even be selected for this purpose for the cover member. If reagent containers with cover members are used to form the reagent container assembly, it may therefore be advantageous when the welding process is carried out on the cover members.

Embodiments of the invention also concern a reagent container assembly such as one that can be produced, for example, by a process according to an embodiment of the invention. Such a reagent container assembly is characterized in that the reagent containers are permanently joined together by at least one fusion welding spot.

In this embodiment, the reagent containers of the reagent container assembly can be solely joined together directly via their outer walls by common fusion welding spots or be brought together in a common stand and welded with this stand.

If reagent containers with a cover member are used, it may be advantageous if the reagent containers are joined together via their cover members by means of the fusion welding spot.

In order to prevent or minimize the reagents filled into the reagent containers from being damaged by the heat generated during the ultrasonic welding, it can be provided that the reagent container assembly has at least two reagent containers in which each has at least one plate-shaped connecting wall section with an outwardly protruding plate edge, wherein the connecting wall sections of the two reagent containers in the reagent container assembly rest against one another at least in the area of their respective plate edges or run essentially parallel to one another with a small spacing, and wherein the two reagent containers are permanently joined together at the two connecting wall sections by at least one weld and in particular, a welded joint.

Embodiments of the present invention are described in detail hereafter with reference to the attached drawings.

FIG. 1 shows a reagent container assembly generally referred to by the reference numeral 10. The reagent container assembly 10 comprises reagent containers 12a, 12b, 12c and in which each consist of a cover member 14 and a lower part 16 and are, for example, manufactured from polypropylene. Before the group of reagent containers 12a, 12b, 12c was assembled, they were individually pre-treated by, for example, filling them with different reagents or auxiliary substances.

In the case of a special reagent container assembly, the reagent containers 12a and 12b may consist of pigmented polypropylene which protects the reagents in the interior of the reagent containers 12a, 12b against light. The reagent container 12c that is intended to hold beads may consist of unpigmented polypropylene which has surface properties that are especially suitable for beads. The container 12c could also have an inner coating which further reduces the adhesion of beads to the inner surface of the container.

The cover member 14 comprises a cover which can be lifted by an analyzer so that the respective reagent container 12a, 12b, 12c is opened. The reagent containers 12a, 12b, 12c may have an essentially quadratic cross-section and are joined to form the reagent container assembly 10, which has an essentially rectangular cross-section with the same breadth as one of the reagent containers 12a, 12b, 12c but is three times as wide.

The overlapping side faces of the reagent containers 12a, 12b, 12c adjoin each other in the width direction. Various potential spot-welded joints or spot welds 18, 20, 22, 24 are shown in FIG. 1 on edges of the reagent containers 12a, 12b, 12c which are located on these side faces. The spot welds 18, 20, 22, 24 do not, however, all have to be made. For example, two of the reagent containers 12a, 12b, 12c may only be directly joined together via their cover members 14 by a spot weld 18. The joint can, however, also be welded by a spot weld 20 at the upper end of the lower part 16, by a spot weld 22 in the middle or a spot weld 24 at the lower end.

Spot welds corresponding to those opposite to the spot welds 18, 20, 22, 24 may be present on the opposite side of the reagent container assembly 10 that is not visible in FIG. 1 in order to join the three reagent containers 12a, 12b, 12c.

Figure 2:
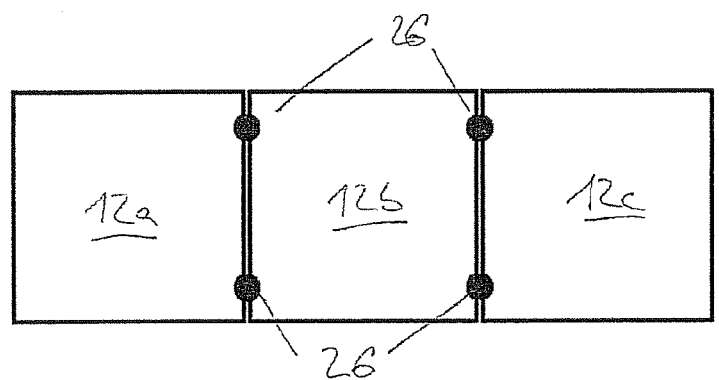
FIG. 2 shows a bottom view of the reagent container assembly of FIG. 1.

FIG. 2 shows the reagent container assembly 10 of FIG. 1 from below. The lower sides of the reagent containers 12a, 12b and 12c can also be directly joined together by spot welds 26. In this case, the welding process takes place on the contiguous edges of the undersides of the reagent containers 12a, 12b and 12c.

Insofar as further embodiment examples are shown in the following figures, their components are labeled by reference numerals which are derived from the reference numerals of the corresponding components of the first embodiment example by adding the numbers 100, 200, etc. The additional embodiment examples are only described insofar as they differ from the first embodiment example to the above description of which reference is otherwise made.

Figure 3:
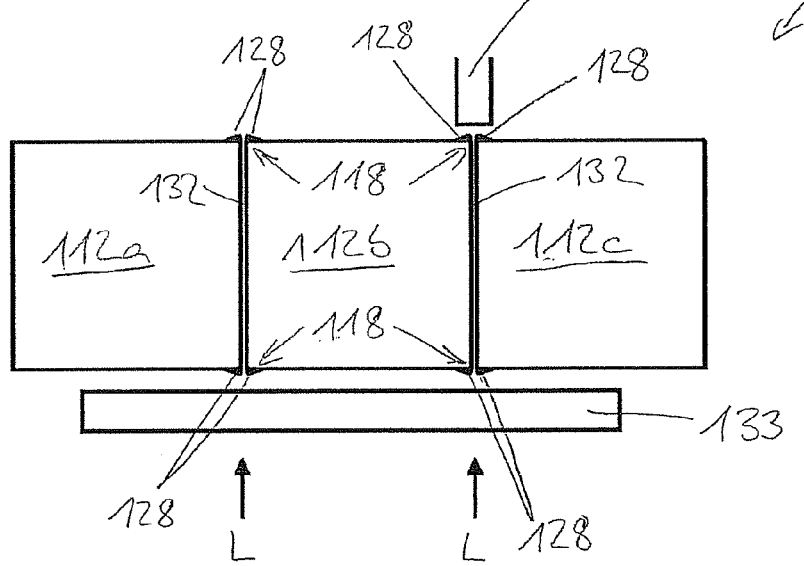
FIG. 3 shows a cross-section through three reagent containers arranged for joining in an alternative embodiment to the reagent containers of FIG. 1.

FIG. 3 shows a cross-section through three reagent containers 112a, 112b and 112c arranged for joining in an alternative embodiment to the reagent containers 12a, 12b, 12c from FIG. 1. Whereas the reagent containers 12a, 12b, 12c consist of essentially plate-shaped plastic walls in the area of the joints 18, 20, 22, 24, 26, the reagent containers 112a, 112b, 112c have material thickenings 128 at the sites where the welding process is to take place in the area of the joints 118. The reagent containers 112a and 112c that are intended to form the two long ends of the resulting container assembly 110 have two material thickenings at the level of the cross-section and the reagent container 112b situated between them has four material thickenings. It is also possible that only one of the reagent containers to be joined at this position has a material thickening in the area of the joint.

The upper part of FIG. 3 shows how the reagent containers 112b and 112c are joined by an ultrasonic welding process. A sonotrode 130 which is for example excited by a piezo element to high frequency oscillations is pressed onto the plastic material of the reagent containers 112b, 112c. The thermoplastic plastic of which the two containers 112b, 112c are manufactured is heated by the high frequency oscillations of the sonotrode and becomes liquid. The material of the reagent container 112b blends with that of the reagent container 112c by the pressure of the sonotrode 130 on the reagent containers 112b and 112c thus resulting in a fusion. After the ultrasonic oscillations have been switched off, the sonotrode 130 still remains according to one variant of the process for some time on the joint 118 until the plastic material solidifies. The welding time is, for example, about 1 to 2 second; the cooling is, for example, about 0.5 to 1 second. The blended plastic material of the two reagent containers 112b and 112c afterwards forms a plastic bridge at the joint 118 which joins the two reagent containers 112b and 112c together.

As will be described further below, a gap 132 may be present between the reagent containers 112a, 112b, 112c due to dimensional tolerances so that the reagent containers 112a, 112b, 112c do not directly rest against one another. In this case, the plastic material liquefied at the joint 118 by the pressure of the sonotrode 130 flows into the gap between the two reagent containers 112b, 112c and forms a bridge after it cools down which joins the two reagent containers 112b, 112c together and keeps the two containers 112b, 112c at a constant distance. Material thickenings 128 are of particular advantage for spaced-apart reagent containers 112a, 112b, 112c because sufficient material is available to form the bridge between the reagent containers 112a, 112b, 112c.

The lower part of FIG. 3 shows how the reagent containers 112a, 112b, 112c can be alternatively directly joined together by means of laser welding. Pressure is applied to the reagent containers 112a, 112b, 112c by means of a plate 133 that is permeable to laser light L, for example, a glass plate 133. Laser light L is beamed through the glass plate 133 onto the joint 118 and liquefies the plastic material of the reagent containers 112a, 112b, 112c at the joints 118. Similarly to the ultrasonic welding, the material of the reagent containers 112a, 112b, 112c blends together at the joints 118 due to the pressure applied to the joints 118 by the plate 133. If laser light L is no longer irradiated onto the joints 118, the plastic material cools down and in each case, two bridges are formed which join the reagent containers 112a, 112b, 112c together.

Exactly as in laser welding, several joints can be generated during an ultrasonic welding process. For example, several sonotrodes which are arranged exactly like the spot welds that are to be generated, can be pressed simultaneously onto one side of the assembled reagent container assembly.

Also, it is possible in a particularly advantageous manner to join together reagent containers made of different plastic materials by means of an appropriate welding process. This only requires that thermoplastic plastic material is used for the reagent containers to be joined. For example, injection-molded reagent containers made of polypropylene can be welded to extrusion blown reagent containers made of polyethylene.

Figure 4:
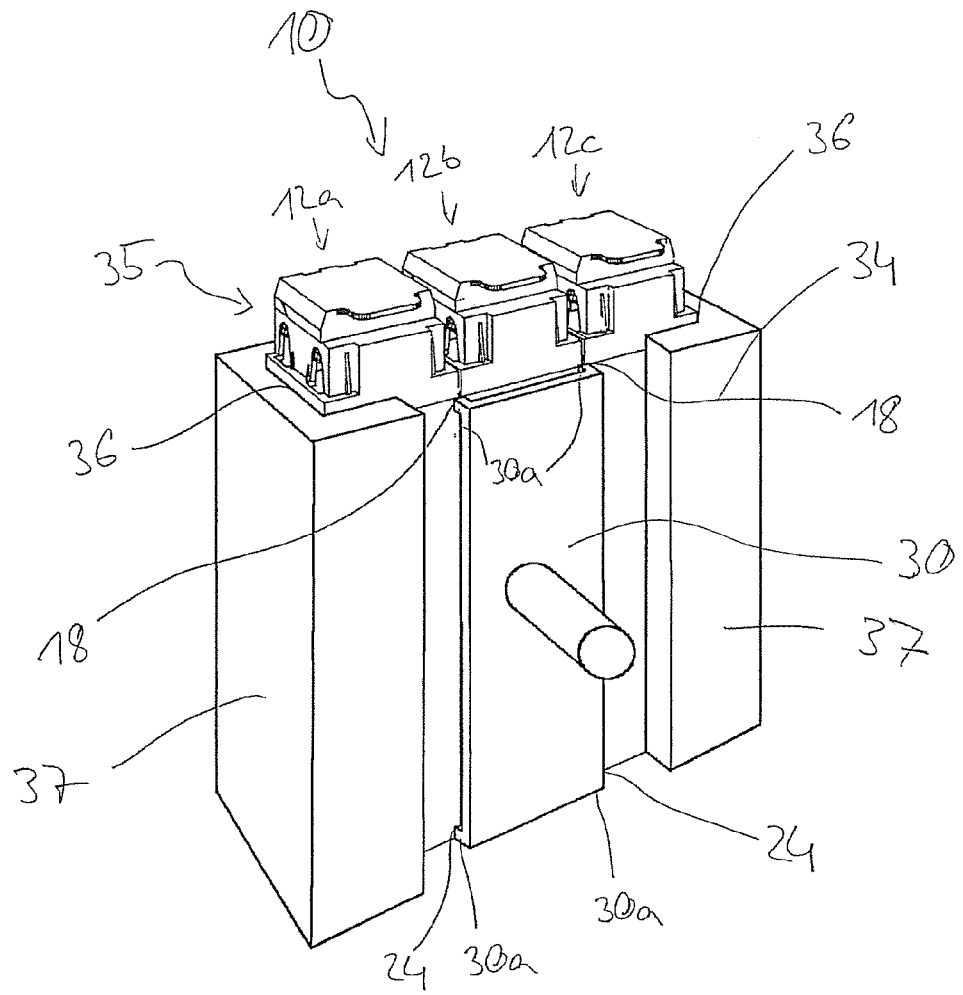
FIG. 4 shows the reagent container assembly of FIG. 1 in a positioning device during an ultrasonic welding process in a perspective view.

FIG. 4 shows the reagent container assembly 10 from FIG. 1 in a positioning device 34 during an ultrasonic welding process in which four welded joints 18, 24 are simultaneously generated on one side of the reagent container assembly 10. This welding process is embedded in a production process for a reagent container assembly which is described hereafter.

Three reagent containers 12a, 12b, 12c filled with different reagents are conveyed by a transport mechanism with a conveyor belt or by a gripper robot to the positioning device 34 and positioned in this device. In a first welding process, a multiple sonotrode 30 with four welding dies 30a is pressed against the side of the reagent container assembly 10. The welding dies 30a can have any suitable shape and thus, for example, have an essentially rectangular cross-section with rounded edges or alternatively also an oval cross-section. In order to achieve a higher rigidity, it is also possible to use a multiple sonotrode comprising for example six to ten or more welding dies.

The three reagent containers 12a, 12b, 12c are arranged successively between two stops 36 of the positioning device 34 during the welding process where the side of the containers facing away from the sonotrode rests against a side stop 35 of positioning device 34 and U-shaped gripping ends 37 of the positioning device 34 grip around the longitudinal ends of the reagent container assembly 10. The reagent containers 12a, 12b, 12c are secured in this manner in well-defined positions during the welding process.

After the first welding and cooling process, which together last about 2.5 to 3 seconds, the reagent container assembly 10 is transported by the transport mechanism with a conveyor belt or the gripper robot to a second positioning device 34 and placed in the second positioning device 34 with the already welded side against the side stop 35. Alternatively, the reagent container assembly 10 can also be rotated 180° by the gripper robot in the first positioning device 34. Then a second welding process is carried out analogously to the first welding process in which the other side of the reagent container assembly 10 is welded with the multiple sonotrode 30. After a second cooling process, the reagent container assembly 10 which is now welded on both sides is transported to subsequent stations at which, for example, a labeling is carried out or an RFID chip is attached to the reagent container assembly 10.

According to a further variant of the process, it is also possible that the reagent containers of the reagent container assembly are welded together by two or more sonotrode arrangements on opposite sides, e.g., simultaneously.

Figure 5:
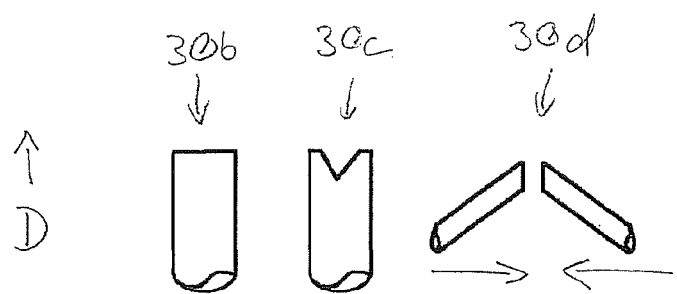
FIG. 5 shows diagrammatically three embodiments of welding dies for a sonotrode.

FIG. 5 shows further possible embodiments of possible welding dies 30b, 30c, 30d for a multiple or single sonotrode 30 which is pressed onto the welding spot in direction D. The welding die 30b has a flat essentially circular or ellipsoidal welding surface. The welding die 30c has a similar shape to the welding die 30b but in this embodiment has a V-shaped depression in its end region which facilitates the blending of the liquid plastic material. By pressing in direction D, the V-shaped depression has the effect that the liquefied plastic material is pressed towards the central plane of symmetry of the welding die 30c. The sonotrode 30d, which consists of two elements which move towards one another when pressed in direction D, has the same effect.

Figure 6:
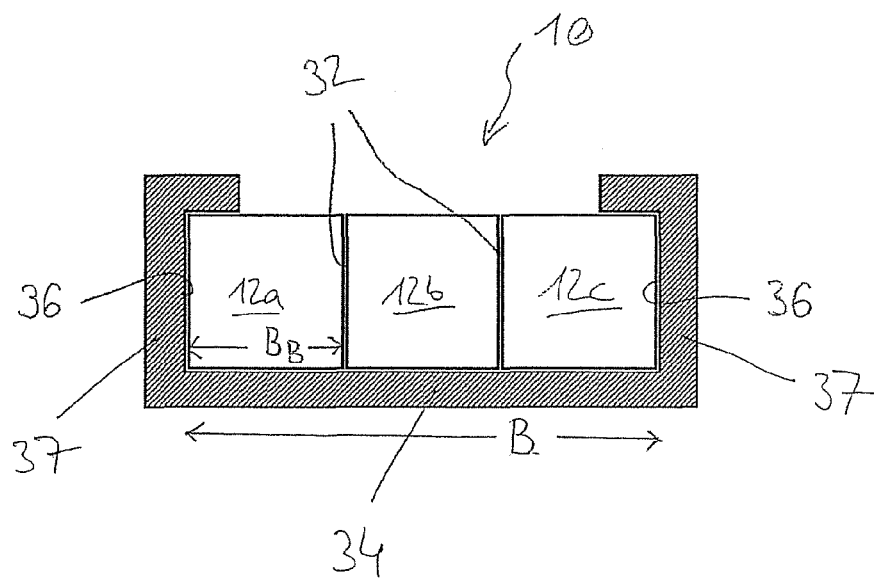
FIG. 6 shows a cross-section through the reagent container of FIG. 4 arranged in a positioning device.

FIG. 6 shows a cross-section through the positioning device of FIG. 4 in which the three reagent containers 12a, 12b, 12c are arranged. As described further, it is advantageous when the reagent container assembly 10 has a defined width B so that the analyzer receiving this reagent container assembly 10 can position the openings of the reagent containers 12a, 12c at the ends of the reagent container assembly 10 as exactly as possible.

In order to produce a reagent container assembly 10 with a predefined width B, the reagent containers 12a and 12c are arranged in the positioning device 34 in such a manner that one side face rests against positioning stops 36 of the positioning device 34. The reagent containers 12a and 12c are preferably pressed against the positioning stops 36 during the welding. The reagent container 12b is centered between the two reagent containers 12a, 12c. The distance between the positioning stops 36 is preset to the width B. The width $B_B$ of the reagent containers 12a, 12b, 12c has a production-related variance. The reagent containers 12a, 12b, 12c shown in FIG. 6, for example, have a quadratic cross-section with a width $B_B$ of 28 mm and in each case a tolerance of +/−0.2 mm. If the reagent containers 12a, 12b, 12c were to be arranged with side faces resting against one another, this would result in an overall width B of the reagent container assembly 10 of 84+/−0.6 mm. This varying total width B of the reagent container assembly 10 can now be compensated by the positioning of the reagent containers 12a, 12b, 12c in the positioning device 34.

However, there may then be a gap 32 between the reagent containers 12a, 12b, 12c. However, as already mentioned, firm bridges are formed by the welding process at the points where the reagent containers 12a, 12b, 12c are connected which hold the reagent containers at the distance set in the positioning device 34.

If, in contrast to the process that has just been described, a reagent container assembly is generated without an exactly pre-defined width, it is advantageous when the reagent containers resting against one another are arranged during the welding in a holder in such a manner that the welding die strikes the junctions between the reagent containers to be joined as centrally as possible. This can, for example, be achieved in the case of a reagent container assembly consisting of three reagent containers by firstly arranging the middle reagent container in the middle of the holder and pressing on the two outer reagent containers from both sides. Alternatively, several reagent containers can be pressed together from both sides by a pre-defined force in the width direction of the reagent container assembly such that the reagent container assembly is centered relative to the sonotrode arrangement.

Figure 7:
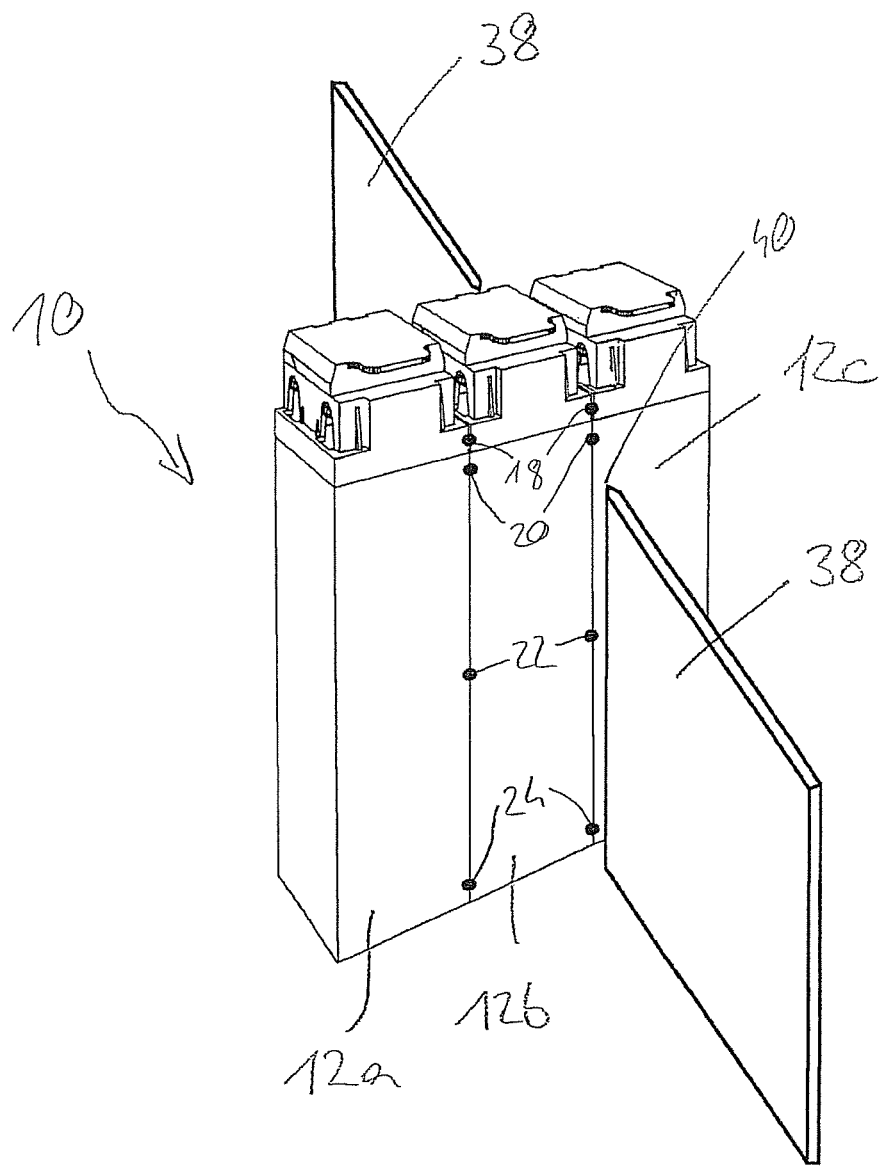
FIG. 7 shows the reagent container assembly of FIG. 1 together with two knives for separating a reagent container.

FIG. 7 shows how the reagent container 12c can be again automatically separated from the reagent container assembly 10. The welds 18, 20, 22, 24 between the reagent container 12b and the reagent container 12c can be broken by a knife 38 (whose end or edge 40 facing the reagent container assembly 10 can be pointed), by using the edge 40 to cut or fracture the bridges that have formed there between the two containers 12b, 12c. The knife 38 is, for example, a 1 mm thick sheet of steel.

FIG. 8 shows a further embodiment of a reagent container 212a with a cover member 214. The lower part 216 of the reagent container 212a has a rounded lower end and thus the reagent container 212a cannot stand alone on a flat surface.

FIG. 9 shows how three such reagent containers 212a, 212b, 212c can be arranged together in a stand or base box 240 and welded thereto such that a further embodiment of a reagent container assembly 210 is formed which can stand on its own on a flat support. In this case, the reagent containers 212a and 212b are joined together at a common spot weld 218a and are also at the same time joined to the stand 214. The reagent containers 212b and 212c in turn have no common welds but rather are indirectly joined together by means of the stand 240 via the spot welds 218a, 218b, 218c.

Figure 10:
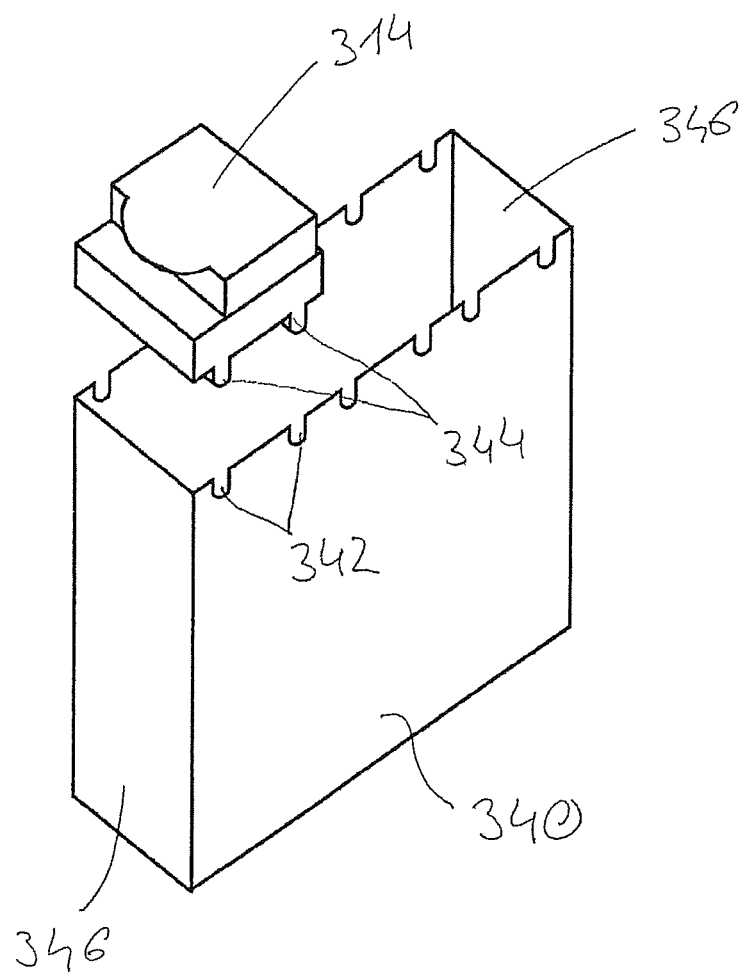
FIG. 10 shows a further embodiment of a stand which also serves to position the reagent containers arranged therein.

FIG. 10 shows how a stand 340 can also be used to position reagent containers. For this purpose, recesses 342 are provided in the stand 340 into which projections 344 of a cover member 314 can be inserted. The projections 344 and the recesses 342 have the same width in the longitudinal direction of the reagent container assembly. Hence, the cover member 314 in which the opening of the associated reagent container is also located, can no longer slip in the longitudinal direction of the stand 340 during the welding process. The opening in the cover member 314 is secured relative to the side walls 346 of the stand 340.

FIG. 11 shows a further embodiment of reagent containers 412a, 412b, 412c which can be welded by ultrasonic welding using a special multiple sonotrode 430, which is also shown to form a further embodiment of a reagent container assembly 410 (cf FIG. 14).

In FIG. 11 the individual reagent containers 412a, 412b, 412c are not yet prepositioned for ultrasonic welding but are rather arranged at a larger distance from one another in order to better discern the structure of the individual containers. In the interest of clarity, the individual components of the reagent containers 412a, 412b, 412c are only labeled with reference numerals on one of the containers 412c as an example. Even if a structural element occurs several times in a figure, not all corresponding structural elements are marked with reference numerals.

Each of the reagent containers 412a, 412b, 412c has a lower member 416 and a cover member 414. The lower member 416 comprises the actual reagent holder 415 as well as two plate-shaped side walls 417 which face one another and run parallel to one another, and between which the reagent holder 415 is arranged. The side walls 417 and the reagent holder 415 are joined together by several horizontal stabilizing structures 419. The reagent holder 415, side walls 417 and stabilizing structures 419 can be manufactured in one piece from plastic in a suitable molding process.

Each of the side walls 417 comprises the connecting wall sections 417a with outwardly protruding plate edges 417k. Since the connecting wall sections 417a are not in direct contact with the reagent holders 415, particularly firm ultrasonic welding joints can be made at the connecting wall sections 417a of neighboring reagent containers without risking damage to the reagent holder 415 or to the reagent filled into the reagent holder 415. In particular, filled and capped reagent containers 412a, 412b, 412c can be assembled to form a reagent container assembly.

For this purpose, the reagent containers 412a, 412b, 412c are firstly arranged as shown in FIG. 12 in such a manner that connecting wall sections 417a of in each case two neighboring reagent containers 412a and 412b or 412b and 412c rest directly against one another or at least are parallel to one another with a small spacing.

As illustrated in FIG. 13, the multiple sonotrode 430 can be pressed against the reagent containers in direction D such that the welding die 430e of the multiple sonotrode 430 in each case engages around two plate edges of the adjacent or parallel connecting wall sections 417a of the side walls 417 and permanently connects them together by a combination of high frequency oscillations and pressure.

The welding dies 430, of which one is shown in FIG. 16 in a different perspective view and magnified, are designed such that they engage around the connecting wall sections 417 over a distance s in the longitudinal direction L of the reagent containers 412a, 412b, 412c, and thus each form a welded joint 421 of length s as shown in FIG. 14, which shows the reagent container assembly 410 and the multiple sonotrode 430 after the welding process. FIG. 15 shows an enlargement of a section of the area referred to as A in FIG. 14 in which the welded joints 421 are easier to see.

The longitudinal end region 430a of the welding die 430, which engages around the connecting wall sections 417a during the welding process, is similar to the welding die 30c from FIG. 5 and is configured in the form of a rounded V. In this manner, the connecting wall sections 417a are pressed simultaneously together when the welding die 430e exerts pressure in the direction D which increases the joint strength of the weld 421.

In the illustrated embodiment example, neighboring reagent containers 412a and 412b or 412b and 412c are each joined together by four welded joints 421, but only the generation of welded joints on one side S1 of the reagent container assembly 410 is shown in FIGS. 11-14 which, however, can also be carried out in the same manner on the other side S2 (for example, by rotating the assembly by 180°).

Due to the sonotrode arrangement of the multiple sonotrode 430, it is possible to simultaneously weld together the three reagent containers 412a, 412b, 412c on one of the two sides S1, S2.

A positioning device is not shown in FIGS. 11 to 14 only for reasons of clarity. In this case, it is possible to use a similar positioning device as for example shown in FIG. 4.

A reagent container assembly having an essentially rectangular cross-section and comprising three reagent containers has been shown in the previous embodiment examples. However, the process for joining reagent containers by welding is not limited to such reagent container assemblies and the embodiments shown of reagent containers. Reagent container assemblies comprising two to six or more containers can also be achieved without difficulty. The reagent container assembly can also have a trapezoidal or wedge-shaped cross-section as is advantageous especially for reagent rotors. It is also possible to use single-walled and double-walled reagent containers of any external design. For example, reagent containers having a round cross-section or at least having rounded side faces, which only rest against one another along a line, can be welded together.

What is claimed is:

1. A process for producing a reagent container assembly made of plastic comprising:
   assembling a group of particular reagent containers; and
   joining the reagent containers to form the reagent container assembly such that at least two of the reagent containers are joined together by at least one welding process,
   wherein before the reagent containers are joined to form the reagent container assembly, said process comprises filling at least one of the particular reagent containers with a first reagent,
   wherein before the reagent containers are joined to form the reagent container assembly, said process comprises filling at least one other of the particular reagent containers with at least one other reagent which is calibrated against the first reagent,
   wherein before the step of filling the at least one other reagent container, said process comprises calibrating the at least one other reagent against the first reagent,
   said process further comprises:
   collecting calibration data during the calibration of the at least one other reagent against the first reagent; and
   providing the reagent container assembly with the calibration data in a form which can be read-out by the user or automatically read-out by an analytical system with a bar code or RFID transponder; and
   wherein the at least two reagent containers to be joined together are used which each have a plate-shaped connecting wall section with an outwardly protruding plate edge, wherein the two reagent containers are arranged before joining in such a manner that the connecting wall sections rest against one another at least in the area of the plate edges or are essentially parallel to one another with a small spacing and wherein the at least two reagent containers are joined via their connecting wall sections by ultrasonic welding with a sonotrode the welding dies of which jointly grip around the two plate edges of the connecting wall sections of the at least two reagent containers during the welding process.

2. A process for producing a reagent container assembly made of plastic comprising:
   assembling a group of particular reagent containers; and
   joining the reagent containers to form the reagent container assembly such that at least two of the reagent containers are joined together by at least one welding process, wherein the welding process is an ultrasonic welding process,
   and wherein at least two reagent containers to be joined together are used which each have a plate-shaped connecting wall section with an outwardly protruding plate edge, wherein the two reagent containers are arranged before joining in such a manner that the connecting wall sections rest against one another at least in the area of the plate edges or are essentially parallel to one another with a small spacing and wherein the two reagent containers are joined via their connecting wall sections by ultrasonic welding with a sonotrode, the welding dies of which jointly grip around the two plate edges of the connecting wall sections of the two reagent containers during the welding process.

3. The process according to claim 1, wherein the welding process is an ultrasonic welding process.

4. The process according to claim 2, wherein the welding process is a laser welding process.

5. The process according to claim 2, wherein a material thickening at which the welding process takes place, is provided on at least one reagent container.

6. The process according to claim 2, wherein the reagent containers are assembled in a common stand and welded to the stand.

7. The process according to claim 6, wherein at least two reagent containers and the stand are welded together with at least one common joint.

8. The process according to claim 2, wherein the reagent containers are assembled and welded together in a positioning device relative to positioning stops of this positioning device.

9. The process according to claim 2, wherein reagent containers with cover members are used to form the reagent container assembly wherein the welding process takes place on the cover members.

10. The process according to claim 2, wherein at least one spot-welded joined is formed during the welding process.

* * * * *